US012005162B2

(12) United States Patent
Eade et al.

(10) Patent No.: US 12,005,162 B2
(45) Date of Patent: Jun. 11, 2024

(54) PROCESS FOR VEHICLE INTERIOR DEODORIZATION

(71) Applicant: Get Spiffy, Inc., Durham, NC (US)

(72) Inventors: Ryan Eade, Durham, NC (US); Zach Fearnside, Durham, NC (US); Mark Welker, Durham, NC (US); Garrett Pell, Durham, NC (US)

(*) Notice: Subject to any disclaimer, the term of this patent is extended or adjusted under 35 U.S.C. 154(b) by 0 days.

(21) Appl. No.: 18/313,231

(22) Filed: May 5, 2023

(65) Prior Publication Data

US 2024/0157015 A1 May 16, 2024

Related U.S. Application Data

(62) Division of application No. 17/986,122, filed on Nov. 14, 2022.

(51) Int. Cl.
*A61L 9/12* (2006.01)
*A61L 9/04* (2006.01)

(52) U.S. Cl.
CPC .................. *A61L 9/12* (2013.01); *A61L 9/046* (2013.01); *A61L 2209/11* (2013.01); *A61L 2209/135* (2013.01)

(58) Field of Classification Search
CPC ........ A61L 9/12; A61L 9/046; A61L 2209/11; A61L 2209/135
See application file for complete search history.

(56) References Cited

U.S. PATENT DOCUMENTS 10,165,906 B1* 1/2019 Beychok .................. A61L 9/12

* cited by examiner

*Primary Examiner* — Sean E Conley
*Assistant Examiner* — Brendan A Hensel

(57) ABSTRACT

The vehicle interior deodorizer may comprise a deodorizing device for deodorizing the interior of a vehicle and a method of using the deodorizing device. During a treatment cycle, the deodorizing device may release a chemical tablet into a cup holding water after an evacuation interval. The chemical tablet may dissolve in the water, creating a deodorizing solution. A bubbler mechanism may de-gas the deodorizing solution and may force deodorizing gas out of the deodorizing device such that the deodorizing gas may saturate the interior of the vehicle during a treatment interval. The bubbler mechanism may quiesce during a dissipation interval such that the deodorizing gas may abate. The vehicle may be opened and aired out to complete the treatment cycle.

8 Claims, 6 Drawing Sheets

PROCESS FOR VEHICLE INTERIOR DEODORIZATION

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

CROSS-REFERENCE TO RELATED APPLICATION

This application claims the benefit of priority as a Divisional application of U.S. Non-Provisional application Ser. No. 17/986,122, filed Nov. 14, 2022, entitled "Vehicle Interior Deodorizer" which is incorporated by reference herein in its entirety.

BACKGROUND

Lingering odors may be considered a leading cause of negative customer feedback for fleet and rental car companies. Odors may often be caused by organic materials, smoke molecules, and bacteria left in a vehicle after use. Chlorine dioxide gas is known to be an oxidizing biocide which excels as a deodorizing agent in enclosed spaced such as vehicle interiors.

BRIEF DESCRIPTION OF THE DRAWINGS

Certain illustrative embodiments illustrating organization and method of operation, together with objects and advantages may be best understood by reference to the detailed description that follows taken in conjunction with the accompanying drawings in which.

DETAILED DESCRIPTION

Figure 1:
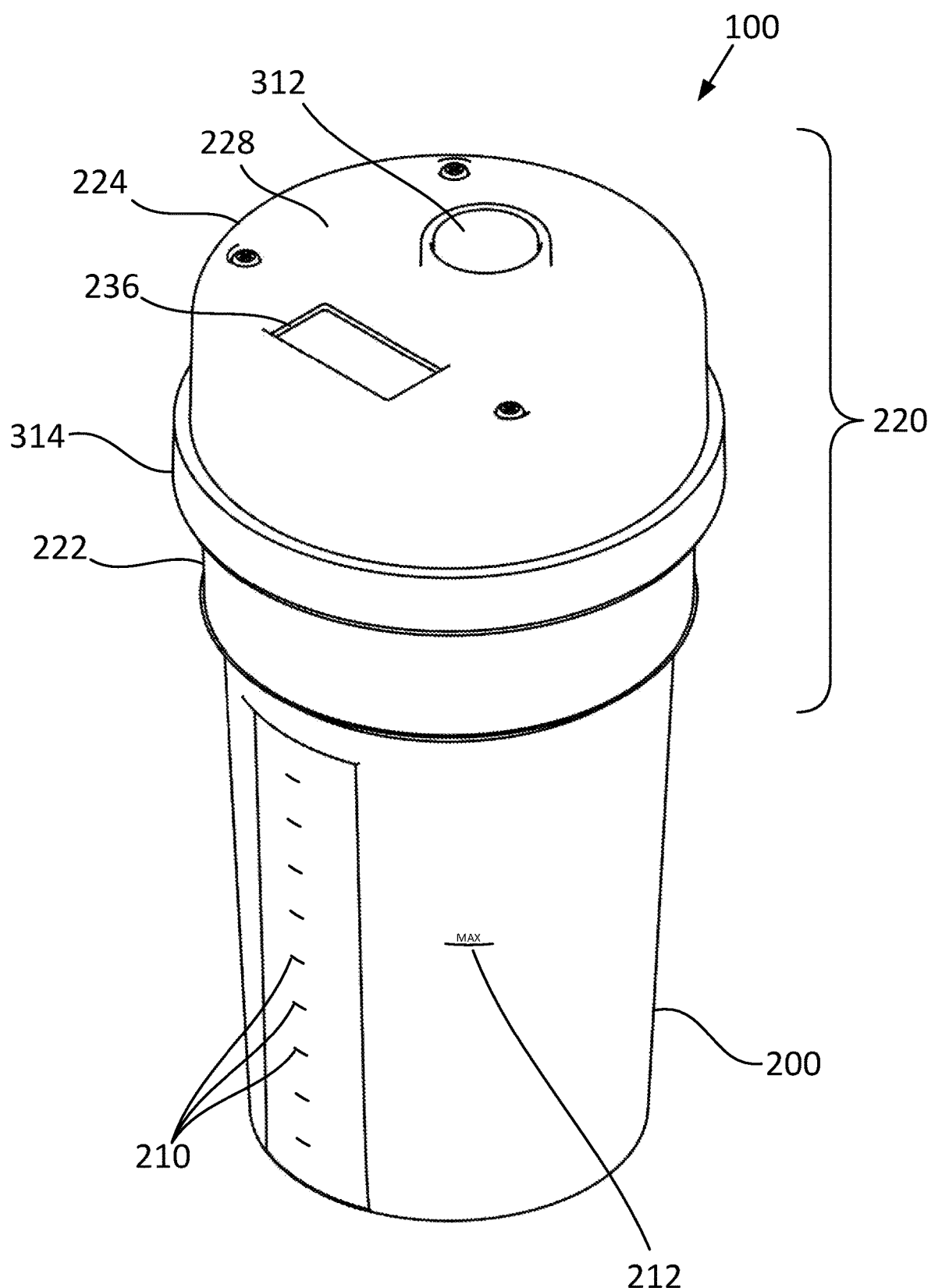
FIG. 1 is an isometric view of a deodorizing device consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The vehicle interior deodorizer (hereinafter invention) comprises a deodorizing device for deodorizing the interior of a vehicle and a method of using the deodorizing device. During a treatment cycle, the deodorizing device may release a chemical tablet into a cup holding water after an evacuation interval. The chemical tablet may dissolve in the water, creating a deodorizing solution. A bubbler mechanism may de-gas the deodorizing solution and may force deodorizing gas out of the deodorizing device such that the deodorizing gas may saturate the interior of the vehicle during a treatment interval. The bubbler mechanism may quiesce during a dissipation interval such that the deodorizing gas may abate. The vehicle may be opened and aired out to complete the treatment cycle.

The deodorizing device may comprise the cup and a lid. The cup may be an open-top container for holding the water and may be configured to fit within a cup holder of the vehicle. The cup may be non-opaque such that the level of the water within the cup may be visible. The cup may comprise a cup sidewall and a cup bottom panel. The top of the cup sidewall may comprise a threaded exterior for coupling to the lid.

The cup may comprise indicia located on the cup sidewall. The indicia may comprise measurement marks, a max fill line, or both. The measurement marks may indicate the volume of the water that is in the cup. As non-limiting examples, the measurement marks may indicate the volume of the water in units of fluid ounces, milliliters, or both.

The max fill line may indicate the volume of the water that may comprise a proper fill level for the treatment cycle. As a non-limiting example, the max fill line may be 8 fluid ounces.

The lid may detachably couple to the top of the cup during the treatment cycle. The lid may house a tablet release mechanism, the bubbler mechanism, a controller, one or more batteries, and operator controls. The lid may comprise a lid top portion and a lid bottom portion. In some embodiments, the lid top portion may separate from the lid bottom portion to provide maintenance access to the interior of the lid. The bottom of the lid bottom portion may comprise a threaded interior. When the lid is coupled to the cup, the lid bottom portion may extend down over the top of the cup such that the threaded interior of the lid bottom portion may engage the threaded exterior of the top of the cup.

The lid may comprise a tablet chamber. The tablet chamber may comprise an aperture that passes entirely through the lid from top to bottom. The chemical tablet may fit entirely within the tablet chamber. The chemical tablet may pass through the tablet chamber into the cup unless retained within the tablet chamber by the tablet release mechanism.

The tablet release mechanism may be operable to retain the chemical tablet within the lid until the end of the evacuation interval. The tablet release mechanism may drop the chemical tablet into the cup at the end of the evacuation interval. The tablet release mechanism may comprise a tablet door, a servomotor, and a tablet sensor.

The tablet door may be an armature located below a lid bottom panel. The tablet door may be coupled to the servomotor and the servomotor may pivot the tablet door between a retain tablet position and a release tablet position. When the tablet door is in the retain tablet position, the tablet door may align with the tablet chamber such that the chemical tablet may be retained within the tablet chamber. When the tablet door is pivoted to the release tablet position, the chemical tablet may be free to fall into the cup.

The servomotor may be an electrical motor that may incorporate a feedback circuit that allows for the angular positioning of the electric motor. The servomotor may pivot the tablet door between the retain tablet position and the release tablet position as commanded by the controller.

The tablet sensor may be operable to sense the presence of the chemical tablet within the tablet chamber. The tablet sensor may be electrically coupled to the controller such that the controller may determine the presence of the chemical tablet within the tablet chamber. As non-limiting examples, the controller may refuse to start the treatment cycle if the chemical tablet is not present in the tablet chamber and the controller may refuse to continue the treatment cycle if the chemical tablet is not verified to have fallen from the tablet chamber when the tablet door is pivoted to the release tablet position.

The tablet sensor may comprise one or more optical sensors. As a non-limiting example, an IR transmitter may transmit a light beam laterally through the tablet chamber to an IR receiver such that the light beam may be interrupted when the chemical tablet is present in the tablet chamber and the light beam may be uninterrupted when the chemical tablet is absent from the tablet chamber. The controller may monitor output of the IR receiver to determine if the chemical tablet is present within the tablet chamber.

The chemical tablet may dissolve in the water to produce the deodorizing solution. In a preferred embodiment, the chemical tablet may be 20 grams of chlorine dioxide.

The bubbler mechanism may de-gas the deodorizing solution by forcing air through the deodorizing solution, thus aerating the deodorizing solution and releasing the deodorizing gas from the deodorizing solution. The bubbler mechanism may increase air pressure within the deodorizing device such that the deodorizing gas may be forced out of the deodorizing device and into the interior of the vehicle. The bubbler mechanism may comprise an air pump, air intake tubing, air outlet tubing, and an air bubbler. When energized, the air pump may move the air from an air intake to an air outlet located under the lid. The air pump may be electromechanical and may comprise an internal motor that may be energized and deenergized as commanded by the controller. As non-limiting examples, the air pump may move the air by applying rotary motion, reciprocating motion, linear motion, or any combination thereof to one or more gears, screws, pistons, shuttle blocks, vanes, diaphragms, plungers, chains, ropes, impellers, or any combination thereof.

The air intake tubing may convey the air from the air intake to the air pump. The air outlet tubing may convey the air from the air pump to the air bubbler and may position the air bubbler at the bottom of the cup.

The air bubbler may aerate the water and may produce a plurality of bubbles. As a non-limiting example, the air bubbler may be a spherical porous stone. The plurality of bubbles produced by the air bubbler may de-gas the deodorizing solution.

The controller may be operable to control the operation of the deodorizing device. As non-limiting examples, the controller may be adapted to interact with a user via the operator controls, command the servomotor to pivot the tablet door, energize and deenergize the air pump, and monitor and report the charge remaining in the one or more batteries.

In some embodiments, the controller may comprise a one-chip microcontroller. The one-chip microcontroller may comprise a processor, non-volatile memory, random access memory, one or more input/output ports, and one or more timers. The non-volatile memory may store processor instructions of a control program that controls the operation of the deodorizing device. The processor may execute the processor instructions of the control program in order to operate the deodorizing device. The random access memory may store transient data and intermediate computations. The one-chip microcontroller may interact with the operator controls, the servomotor, the air pump, and the one or more batteries via the one or more input/output ports. The one-chip microcontroller may time intervals using the one or more timers. As non-limiting examples, the one or more timers may be implemented in hardware or software.

The one or more batteries may comprise one or more energy-storage devices. The one or more batteries may be a source of electrical energy to operate the controller, the operator controls, the servomotor, and the air pump. The one or more batteries may be rechargeable from an external power adapter plugged into a recharging port.

The operator controls may be adapted for the user to control and monitor the deodorizing device. The operator controls may comprise a start/stop button for initiating and terminating the treatment cycle and a light ring for displaying an operational state and device status. The operator controls may be electrically coupled to the controller such that the controller may monitor the start/stop button and may control the light ring.

The start/stop button may be accessible on a lid top panel. The start/stop button may be pressed to start the treatment cycle. If the treatment cycle is in progress, the start/stop button may be pressed to terminate the treatment cycle. In some embodiments, the start/stop button may be covered by a shroud to protect the start/stop button from exposure to moisture. The start/stop button may also have a protective barrier around the button to prevent the start/stop button from being activated during shipping of the device.

The light ring may comprise a plurality of indicators arranged in a horizontal ring surrounding the lid. An individual indicator selected from the plurality of indicators may be a multicolor LED. The on/off state, color, and brightness of the individual indicator may be controlled by the controller. As a non-limiting example, the individual indicators may be individually addressable RGB LEDs.

The controller may activate and deactivate the plurality of indicators individually or in groups. The controller may sequence the activation and deactivation of the plurality of indicators to produce moving patterns of the plurality of indicators. As a non-limiting example, the controller may sequentially activate and deactivate the plurality of indicators to create a chase light effect where one or more of the individual indicators appear to spin around the light ring.

Throughout the remainder of this document, 'spinning' may refer to a blinking sequence of the plurality of indicators that create the chase light effect, including the chase light effects where the number of illuminated and non-illuminated indicators change. 'Counting' may refer to a spinning display where the count of illuminated indicators decreases over time.

'Counting' may comprise an initial state where all of the individual indicators are illuminated and may thus appear to not be moving, however after a delay at least one of the individual indicators may extinguish and may show the chase light effect. Over time, additional indicators may extinguish. 'Solid' may refer to a display of the plurality of indicators where one or more of the plurality of indicators are illuminated and not blinking.

The controller may display the operational state of the deodorizing device using the light ring by selecting a color, pattern, and timing interval for the plurality of indicators. As non-limiting examples:

The controller may display a 'ready to start treatment indication' by illuminating the light ring as solid green indicators for as long as the start/stop button is depressed, up to a maximum set by a ready timeout interval. As a non-limiting example, the ready timeout interval may be 10 seconds. The 'ready to start treatment indication' may indicate that the controller is ready to begin the treatment cycle. The start/stop button should be released while the 'ready to start treatment indication' is displayed on the light ring.

The controller may display a 'countdown indication' by illuminating the light ring as counting yellow indicators for a warning timeout interval following the 'ready to start treatment indication'. As a non-limiting example, the warning timeout interval may be 10 seconds. The 'countdown indication' may indicate that the user should leave the vehicle before the deodorizing gas is released into the interior of the vehicle.

The controller may display a 'treatment in progress indication' by illuminating the light ring as spinning red indicators for a treatment timeout interval following the 'countdown indication'. As a non-limiting example, the treatment timeout interval may be 15 minutes. The 'treatment in progress indication' may indicate that the chemical tablet has been dropped into the cup and the bubbler mechanism is operating to fill the interior of the vehicle with the deodorizing gas. It is not safe for the user to enter the vehicle during the treatment cycle.

The controller may display a 'post treatment wait indication' by illuminating the light ring as counting yellow indicators for a recovery timeout interval following the 'treatment in progress indication'. As a non-limiting example, the recovery timeout interval may be 5 minutes. The 'post treatment wait indication' may indicate that the bubbler mechanism has been deenergized and the deodorizing gas within the vehicle is abating. The user should avoid entering the vehicle during the 'post treatment wait indication'.

The controller may display a 'treatment complete indication' by illuminating the light ring as solid green indicators following the 'post treatment wait indication'. The 'treatment complete indication' may indicate that it is safe to open the vehicle and allow the vehicle to air out.

The controller may display the device status using the light ring by selecting a color, pattern, and timing interval for the plurality of indicators. As non-limiting examples:

The controller may display 'tablet error indication' by illuminating the light ring as solid red indicators. The 'tablet error indication' may indicate that the chemical tablet was not sensed in the tablet chamber prior to beginning the treatment cycle or that the chemical tablet did not drop out of the tablet chamber when the tablet door pivoted to the release tablet position.

The controller may display 'battery level indication' by illuminating the light ring as solid blue indicators. The percentage of the plurality of indicators that are illuminated may correspond to the remaining charge in the one or more batteries. As non-limiting examples, 100% of the plurality of indicators illuminated may correspond to 100% charge remaining, 50% of the plurality of indicators illuminated may correspond to 50% charge remaining, and 5% of the plurality of indicators illuminated may correspond to 5% charge remaining.

The controller may display 'battery charging indication' by illuminating the light ring as solid purple indicators when the external power adapter is plugged into the recharging port. The percentage of the plurality of indicators that are illuminated may correspond to the charge of the one or more batteries. As non-limiting examples, 5% of the plurality of indicators illuminated may correspond to 5% battery charge, 50% of the plurality of indicators illuminated may correspond to 50% battery charge, and 100% of the plurality of indicators illuminated may correspond to 100% battery charge.

The controller may display 'battery low indication' by illuminating the light ring as one (1), two (2), or three (3) solid red indicators. The 'battery low indication' may indicate that the one or more batteries require recharging prior to using the deodorizing device.

The method of using the deodorizing device may comprise the following steps, not necessarily in the order shown:

The user may charge the one or more batteries by plugging the external power adapter into the recharging port until the 'battery level indication' indicates a full charge.

The user may place the water into the cup by removing the lid from the cup, adding the water to the cup up to the max fill line, and replacing the lid on the top of the cup.

The user may place the deodorizing device into the cup holder of the vehicle.

The user may remove the chemical tablet from packaging material and insert the chemical tablet into the tablet chamber accessible at the top of the lid.

The user may prepare the vehicle by starting the engine, turning fans to the highest speed setting, opening all vents, setting the vehicle ventilation system to recirculate the air within the vehicle, and closing all windows.

The user may activate the deodorizing device by pressing the start/stop button, observing the 'ready to start treatment indication', releasing the start/stop button, and observing the 'countdown indication'.

The user may exit the vehicle and close the doors.

The user may observe the 'treatment in progress indication'.

The controller may drop the chemical tablet into the water in the cup by pivoting the tablet door to the release tablet position and may energize the bubbler mechanism.

The user may wait for the treatment cycle to complete. In some embodiments, this may take 15 minutes.

The controller may deenergize the bubbler mechanism.

The user may observe the 'post treatment wait indication'.

The user may wait for the deodorizing gas to abate. In some embodiments, this may take 5 minutes.

The user may observe the 'treatment complete indication'.

The user may open the doors, close vents, turn fans off, and stop the engine.

The user may allow the vehicle to air out.

In an alternative embodiment, the device may provide alternative functionality. In an alternative, the device may have an electrical connection to an outside power source and may not have an internal electrical supply such as a battery. The power system may have a power connection, such as, in non-limiting examples, a usb or "cigarette lighter" connector, to a vehicle in which the device is placed during operation. The vehicle will be running during the operation of the device and will provide a secure, constant source of electricity to the device through the usb or other connector.

In this embodiment, the device may not contain an IR sensor to sense the insertion of a cleansing tablet within the tablet chamber. The insertion of the cleansing tablet is the responsibility of the use in this embodiment, with the device dropping the tablet from the tablet chamber when the drop timer expires in the same fashion as previously described.

In this embodiment, a more limited set of LEDs may communicate via blinking sequences, times, and colors that utilize a more limited set of instructions for either a single LED or a set of LEDs that are fewer in number or limited to a smaller portion of the lid rather than encircling the entirety of the circumference of the device lid. In this embodiment, the user interface for displaying status to a user may be simplified by the removal of the battery level indication.

In an embodiment, additional tablet sensors could consist of laser detection, visible light detection, weight/mass detection, Pneumatic detection, capacitive detection, ultrasonic detection, and/or force detection through the user pressing a bar or button. Additionally, the tablet sensor system may have the ability to detect authentic or allowable disinfectant or deodorizing tablets prior to their insertion in the device. The tablet sensor system may be able to detect authentic tablets through the action of reading barcodes, reading special inks, such as, in non-limiting examples, uv-activated inks, phosphorescent chemicals, or other specialized inks, reading marking or ink patterns, measuring the optical properties of the tablet, measuring the color of the tablet, or measuring the composition of the tablet.

In an embodiment, the device microprocessor provides data collection and communication between components of the device. The microprocessor is active to collect business data from the device during operation of the device and data collected about the device use and performance. Data collected may include information such as the number of services the device is performing, and how many times the device has been activated. The data collected may also include when the services of the device are being performed, where the services are being performed, vehicle information to relate the service to an individual vehicle, and on what specific vehicle the services are being performed through the user interface incorporated into the device. In a non-limiting example, the user input element may be incorporated into the lid of the device.

In an embodiment, the microprocessor may also collect device data that is related to and/or important to the operation and use of the device. In this embodiment the microprocessor may collect information on the current battery charge, battery lifespan, usage information, diagnostic information, and the device lifespan. The microprocessor may also transmit useful business data through either an internal cellular connection or through a Bluetooth application to a phone which may send the business data to an online database. The device may provide a connection to an application installed on a mobile device application that may communicate with the device to relay collected business data from the microprocessor installed within the device.

This application may provide the ability to start and stop the operation of the device from the mobile device through the Bluetooth application connection. The microprocessor may provide the display of business or operational data on the display device installed on the device or may transmit the business or operation data to an exterior device or platform such as a mobile device, laptop, tablet, computer, or other display device exterior to the deodorizing device.

In an embodiment the deodorizing device may be active to detect and track the number of tablets that have been purchased and/or used by a client. The deodorizing device may provide an indication on a display device, or stop working, if the device microprocessor has determined that the client has used more tablets than the client has purchased. This condition may indicate that the client is using unauthorized or non-genuine deodorizing tablets.

In an embodiment, the deodorizing device may be active to use additional cleaning chemicals that are complementary in use to the deodorizing tablets. The device may include a secondary tablet that has fragrances or pleasing odors incorporated within the secondary tablet. The use of the secondary tablet may provide improved and perfumed order in the vehicle when used. Additionally, the fragrance may be added directly to the deodorizing tablet. Alternatively, the device lid may contain a second drop port for the secondary or other fragrance enhanced or scented tablets. The device may have in internal cartridge which meters out a very small amount of scent as a fragrance or improvement to the odor of the interior of the vehicle.

Turning now to FIG. 1, the figure shows an isometric view of the invention 100. The invention 100 may comprise a cup 200 and a lid 220. The cup 200 may comprise indicia 210 to aid in filling the cup 200 with water. The indicia 210 may comprise a max fill line 212 to indicate the proper fill level for use. The lid 220 may comprise a lid top portion 224 and a lid bottom portion 222 that may separate to provide access within the lid 220. The lid bottom portion 222 may overlap the top of the cup 200 such that the lid 220 and the cup 200 may be threadedly coupled. A tablet chamber 236 may pass through the lid 220 from top to bottom. The tablet chamber 236 may be accessible via an aperture on a lid top panel 228. A start/stop button 312 may be accessible on the top of the lid 220. The start/stop button 312 may be operable to start a treatment cycle. A light ring 314 may encircle the lid 220 and may display an operational state and/or device status.

Figure 2:
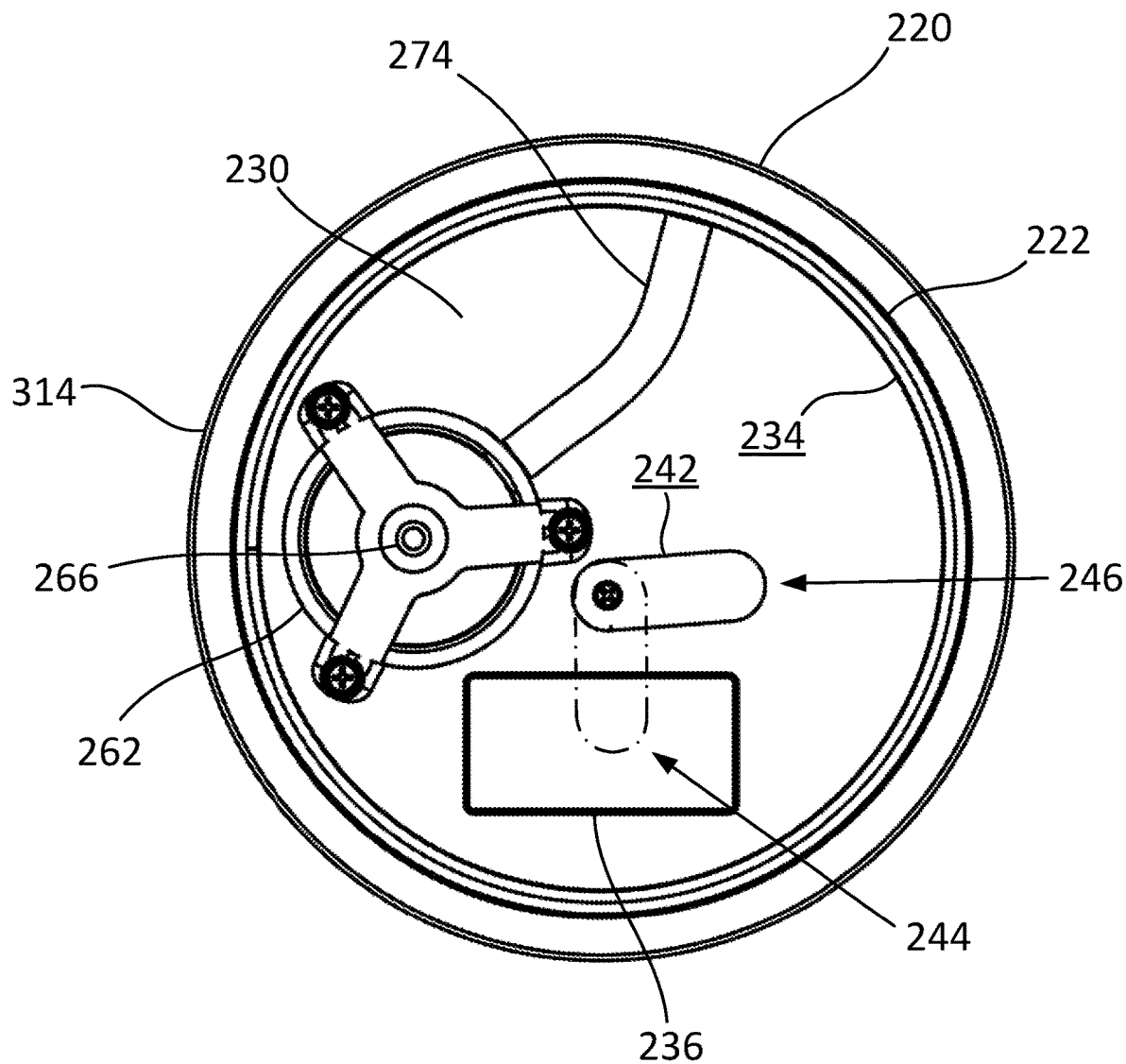
FIG. 2 is a bottom view of a lid consistent with certain embodiments of the present invention.

Turning now to FIG. 2, the figure shows the underside of a lid 220. A tablet chamber 236 opens on the bottom of the lid 220 after passing through the lid 220. A tablet door 242 may be positioned adjacent to the tablet chamber 236. The tablet door 242 may be moveable between a retain tablet position 244 where the tablet door 242 blocks the tablet chamber 236 and a release tablet position 246 where the tablet door 242 does not block the tablet chamber 236. A threaded interior 234 on a lid bottom portion 222 may enable the lid 220 to couple to the cup. An air outlet 266 of an air pump 262 may be exposed beneath the lid 220. Air intake tubing 274 may supply the air pump 262 with air. A light ring 314 may encircle the lid 220 and may display an operational state and/or device status.

Figure 3:
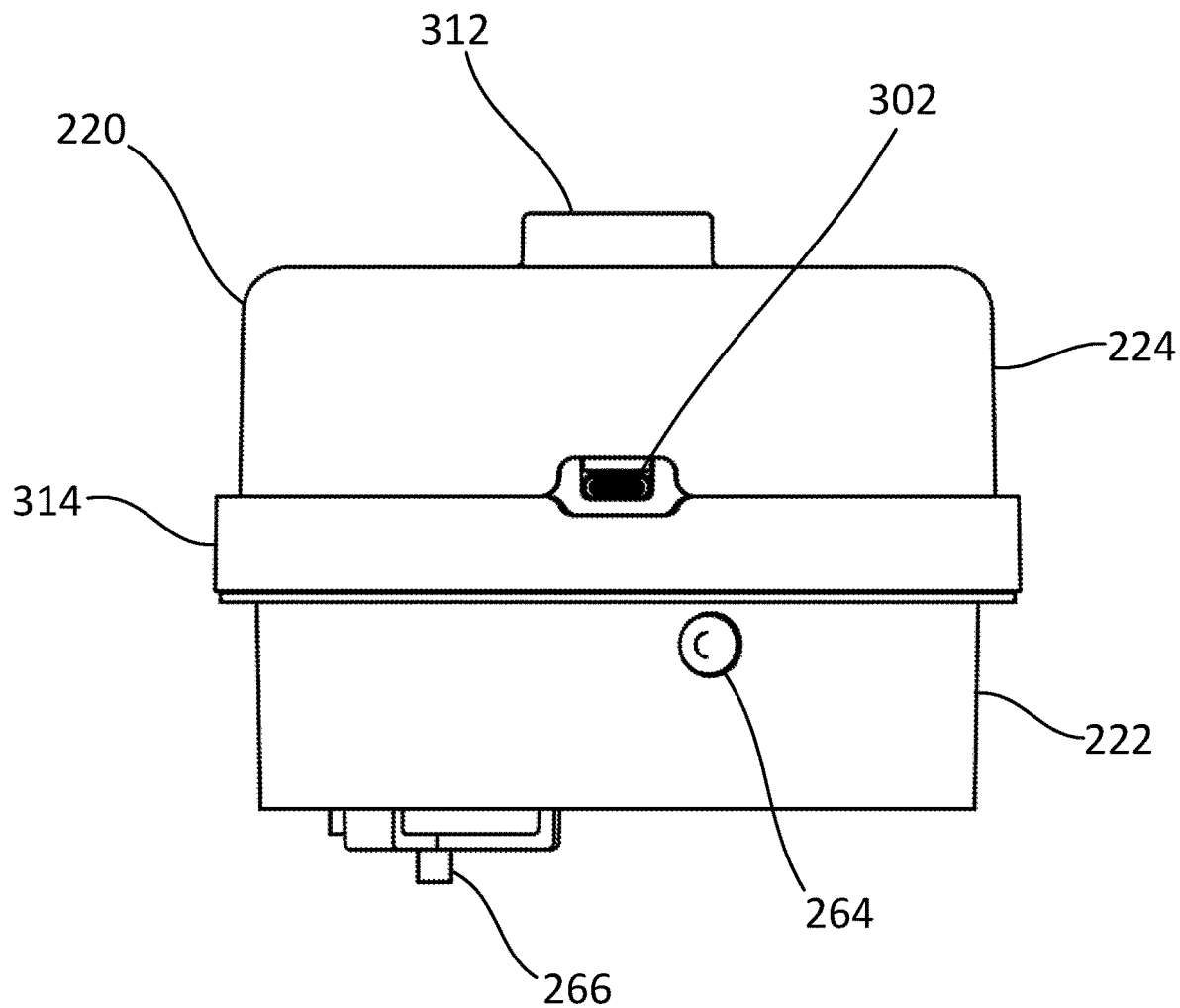
FIG. 3 is a side view of a lid consistent with certain embodiments of the present invention.

Turning now to FIG. 3, the figure shows a side view of a lid 220. The lid 220 may comprise a lid top portion 224 and a lid bottom portion 222. Air may be drawn in via an air intake 264 and may be forced out of an air outlet 266. A start/stop button 312 may be located on top of the lid 220 and a recharging port 302 may be accessible on the side of the lid 220. A light ring 314 may encircle the lid 220 and may display an operational state and/or device status.

Figure 4:
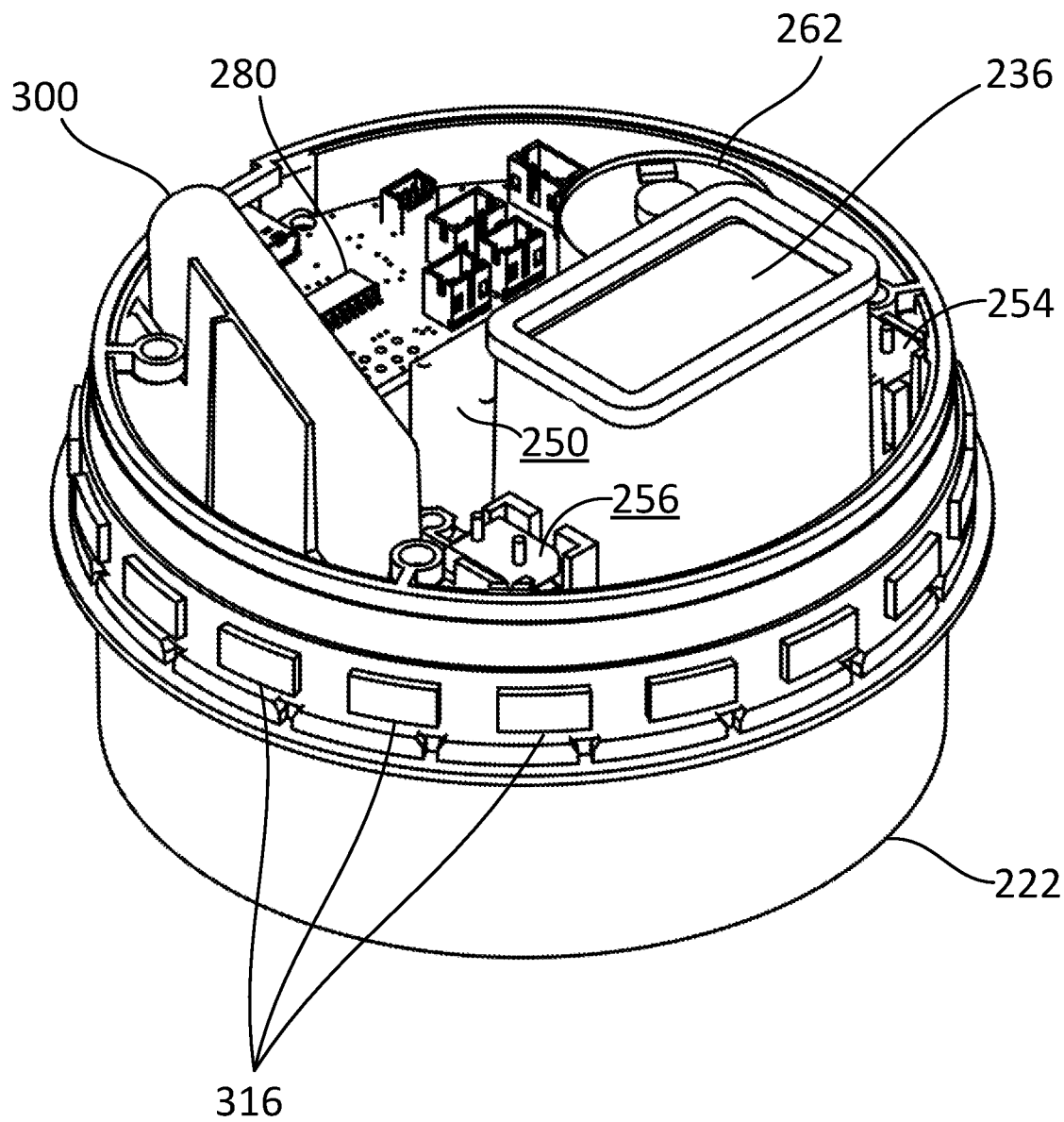
FIG. 4 is a detail view of a lid bottom portion consistent with certain embodiments of the present invention.

Turning now to FIG. 4, the figure shows a detail view of a lid bottom portion 222. An IR transmitter 254 and an IR receiver 256 may be positioned on either side of a tablet chamber 236 in order to detect items within the tablet chamber 236. An air pump 262, one or more batteries 300, a servomotor 250, and a controller 280 may be housed within the lid bottom portion 222. A plurality of indicators 316 comprising the light ring may be seen encircling the lid bottom portion 222.

Figure 5:
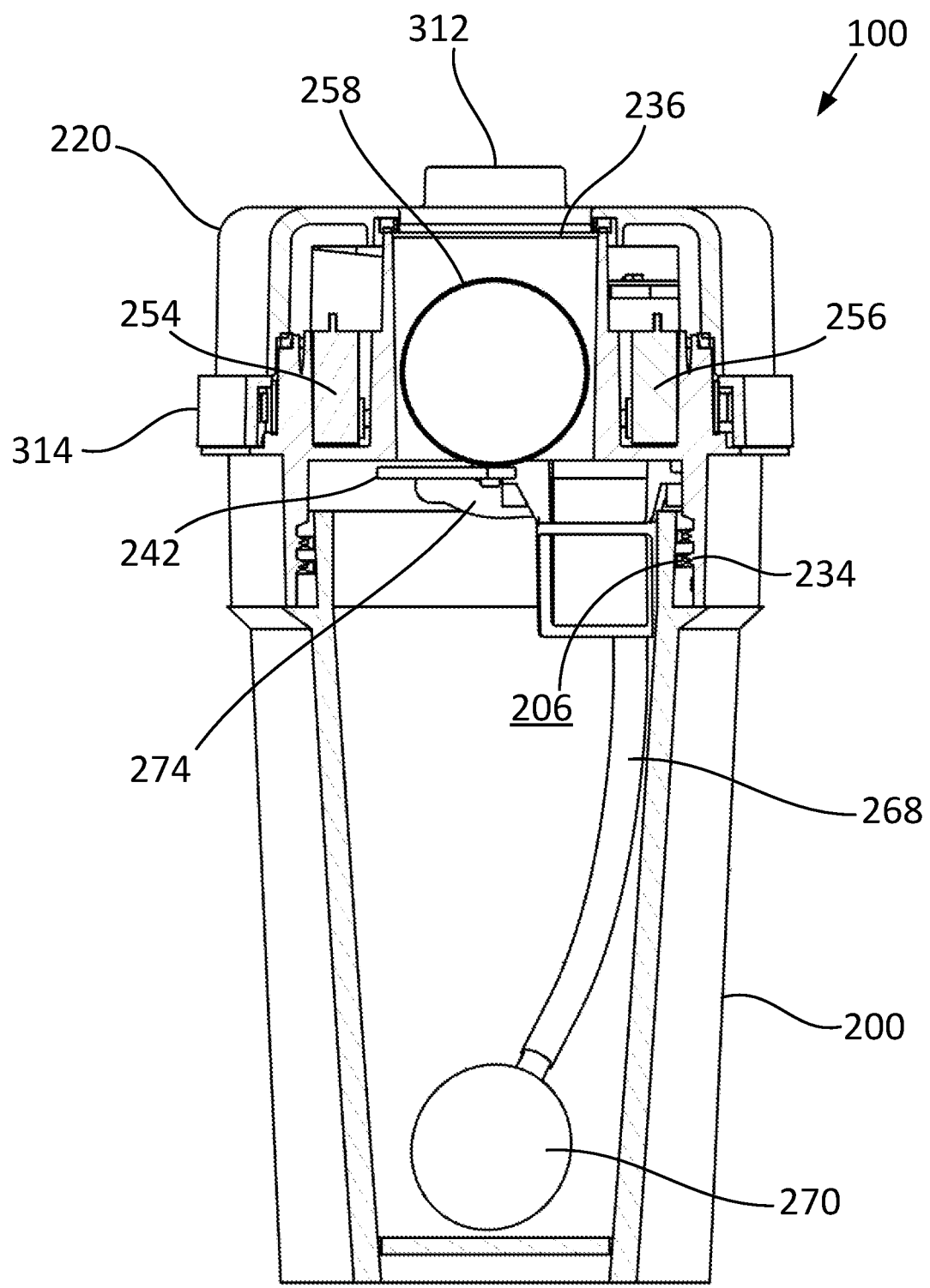
FIG. 5 is a detail side view of a deodorizing device consistent with certain embodiments of the present invention.

Turning now to FIG. 5, the figure shows a detail side view of the invention 100. A threaded interior 234 of a lid 220 may engage a threaded exterior 206 of a cup 200 in order to couple the lid 220 to the cup 200. A chemical tablet 258 may be held within a tablet chamber 236 by a tablet door 242. An IR transmitter 254 and an IR receiver 256 may be positioned on either side of the tablet chamber 236 in order to detect the chemical tablet 258 within the tablet chamber 236. Air drawn into the lid 220 via air intake tubing 274 may be forced into an air bubbler 270 via air outlet tubing 268 to release deodorizing gas. A start/stop button 312 located on top of the lid 220 may be operable to start and stop a treatment cycle. A light ring 314 may encircle the lid 220 and may display an operational state and/or device status.

Figure 6:
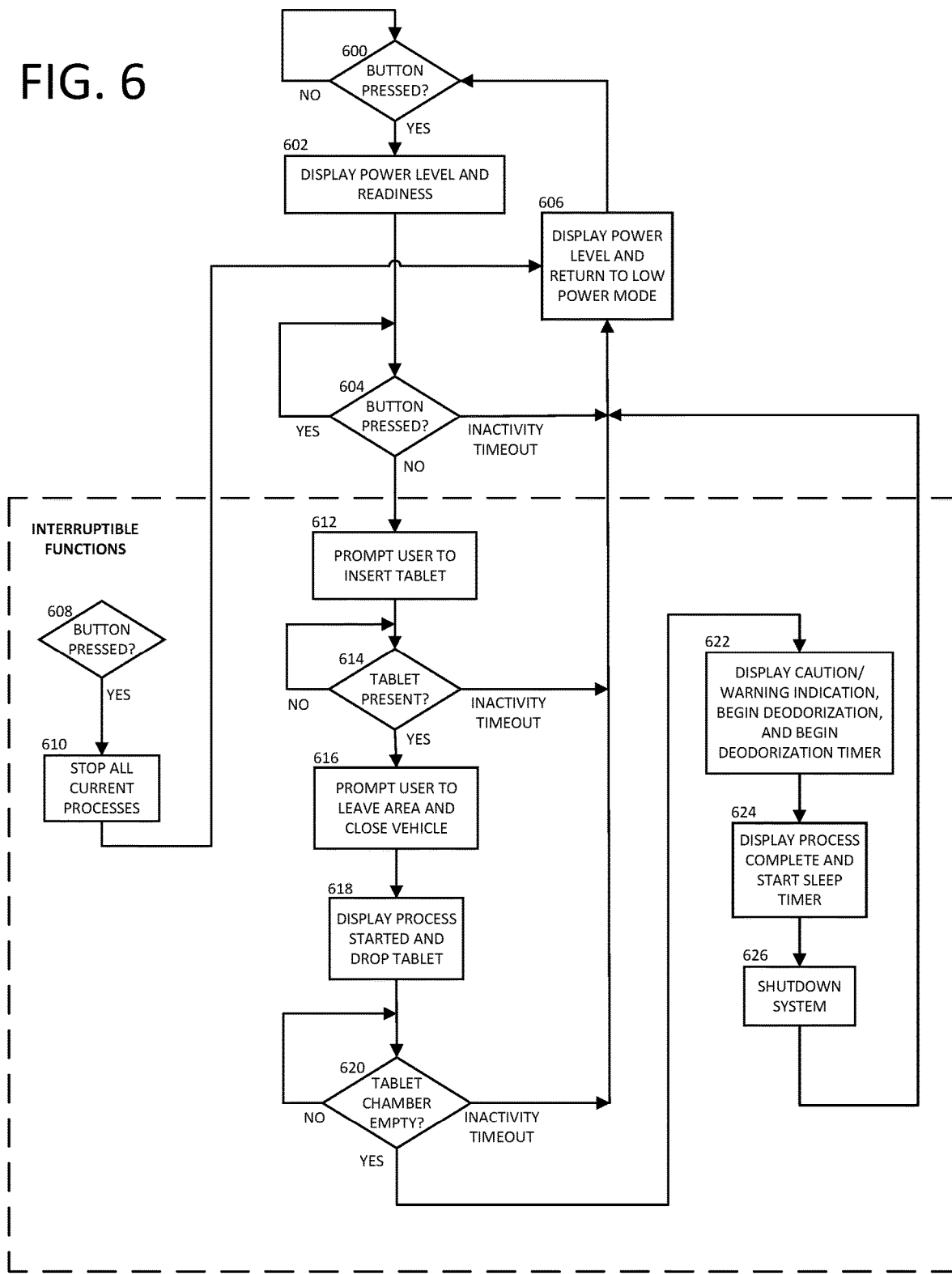
FIG. 6 is a flow diagram for the operation of the deodorizing device consistent with certain embodiments of the present invention.

Turning now to FIG. 6, the figure shows a flow diagram of the operation of an embodiment of the invention. Block 600 forms a loop waiting for depression of the start/stop button. When the start/stop button is pressed, control may pass to block 602 where the light ring may be activated to display 'battery level indication' followed by a 'ready to start treatment indication'. At block 604 control loops waiting for the start/stop button to be released. If the start/stop button is held longer than a ready timeout interval then control may pass to block 606. If the start/stop button is released prior to the ready timeout interval, control may pass to block 612.

At block 606 the invention may return to a low power state with all motors and pumps turned off and the light ring may display the 'battery level indication'. The tablet door may be moved to a retain tablet position. Control may then pass back to block 600.

Block 612 may be one of a number of steps referred to as interruptible functions. As a non-limiting example, interruptible functions may comprise block 612 through block 626. Pressing the start/stop button during an interruptible function may immediately invoke block 608 which passes control to block 610. Block 610 may stop all current processes and may pass control to block 606.

At block 612 a controller may determine if the chemical tablet is present in the tablet chamber and may display 'tablet error indication' if the chemical tablet is not present. Control may then pass to block 614 which may loop while waiting for the chemical tablet to be placed into the tablet chamber. If, at block 614, the chemical tablet is found to be present in the tablet chamber then control, may pass to block 616. If, at block 614, the chemical tablet is not found to be present within a tablet timeout interval then control may pass to block 606. As a non-limiting example, the tablet timeout interval may be 5 minutes.

At block 616, the light ring may display a 'countdown indication' for a warning timeout interval while a user vacates a vehicle. Control may then pass to block 618.

At block 618, the light ring may display a 'treatment in progress indication'. The controller may drop the chemical tablet into water in the cup by moving the tablet door to a release tablet position. Control may then pass to block 620.

Block 620 may loop waiting for an indication that the chemical tablet has fallen out of the tablet chamber. When the tablet chamber is empty, control may pass to block 622. If the tablet timeout interval passes without a determination that the tablet chamber is empty then control may pass to block 606.

At block 622, the controller may energize an air pump to de-gas a deodorizing solution formed by the dissolving tablet and to force the deodorizing gas out of the invention and into the vehicle. At the end of a treatment timeout interval, control may pass to block 624.

At block 624, the light ring may display a 'post treatment wait indication' and may de-energize the air pump. At the end of a recovery timeout interval, control may pass to block 626.

At block 626, the light ring may display a 'treatment complete indication' to indicate that the vehicle is safe to enter.

At the end of a treatment complete timeout interval, control may then pass to block 606. As a non-limiting example, the treatment complete timeout interval may be 10 minutes.

A block 626, the treatment cycle is complete and control may pass to block 606.

While certain illustrative embodiments have been described, it is evident that many alternatives, modifications, permutations and variations will become apparent to those skilled in the art in light of the foregoing description.

What is claimed is:

1. A method of deodorizing a vehicle comprising the steps of:
    placing water into a cup of a deodorizing device by a user;
    placing the deodorizing device into a cup holder of a vehicle by the user;
    inserting a chemical tablet into a tablet chamber accessible at the top of a lid of said deodorizing device by the user;
    said user activating the deodorizing device to initiate a release timer;
    upon expiration of said release timer, the device dropping the chemical tablet into the water in the cup, energizing a bubbler mechanism by a controller, and initiating a treatment cycle;
    at termination of said treatment cycle, said controller deenergizing the bubbler mechanism;
    said device displaying a 'post treatment wait indication' as an indicator of abatement of a deodorizing gas;
    said device displaying a 'treatment complete indication' to the user;
    said user preparing the vehicle for normal use upon completion of the treatment and abatement cycle.

2. The method according to claim 1
    where placing the water into the cup of the deodorizing device comprises the steps of removing the lid from the cup, adding the water to the cup up to a max fill line, and replacing the lid on the top of the cup.

3. The method according to claim 1
    where preparing the vehicle for treatment comprises the steps of starting an engine, turning fans to a highest speed setting, opening all vents, setting a vehicle ventilation system to recirculate air within the vehicle, and closing all windows.

4. The method according to claim 1
    where activating the deodorizing device comprises the steps of pressing a start/stop button, the device displaying a 'ready to start treatment indication', releasing the start/stop button, and the device displaying a 'countdown indication'.

5. The method according to claim 1 where dropping the chemical tablet into the water in the cup comprises the steps of activating a tablet door to a release the tablet position.

6. The method according to claim 1 where preparing the vehicle for normal use comprises the steps of opening the doors, closing vents, turning fans off, and stopping the engine.

7. The method according to claim 1 where control signals are transmitted from the controller to one or more indicator lights to provide visual confirmation to a user of stages of the treatment process.

8. The method according to claim 1 where the controller determines if the chemical tablet is present in the tablet chamber and displaying a 'tablet error indication' if the chemical tablet is not present.

* * * * *